US012141417B1

(12) United States Patent
Douglas et al.

(10) Patent No.: US 12,141,417 B1
(45) Date of Patent: Nov. 12, 2024

(54) METHOD AND APPARATUS OF UTILIZING ARTIFICIAL INTELLIGENCE IN THE SCROLLING PROCESS

(71) Applicants: Robert Edwin Douglas, Winter Park, FL (US); David Byron Douglas, Winter Park, FL (US)

(72) Inventors: Robert Edwin Douglas, Winter Park, FL (US); David Byron Douglas, Winter Park, FL (US)

( * ) Notice: Subject to any disclaimer, the term of this patent is extended or adjusted under 35 U.S.C. 154(b) by 367 days.

(21) Appl. No.: 17/744,694

(22) Filed: May 15, 2022

Related U.S. Application Data

(63) Continuation-in-part of application No. 17/340,023, filed on Jun. 6, 2021, now Pat. No. 11,337,670, and a continuation-in-part of application No. 17/230,959, filed on Apr. 14, 2021, now Pat. No. 11,341,643, which is a continuation-in-part of application No. 16/842,631, filed on Apr. 7, 2020, now Pat. No. 11,003,342, said application No. 17/340,023 is a continuation-in-part of application No. 16/752,691, filed on Jan. 26, 2020, now Pat. No. 11,051,782, said application No. 16/842,631 is a continuation-in-part of application No. 16/594,139, filed on Oct. 7, 2019, now Pat. No. 10,893,844.

(60) Provisional application No. 63/009,997, filed on Apr. 14, 2020, provisional application No. 62/743,837, filed on Oct. 10, 2018.

(51) Int. Cl.
*G06F 3/0482* (2013.01)
*G06F 3/01* (2006.01)
*G06F 3/04845* (2022.01)
*G06F 3/0485* (2022.01)
*G06N 20/20* (2019.01)
*G06T 7/00* (2017.01)

(52) U.S. Cl.
CPC ............ *G06F 3/0482* (2013.01); *G06F 3/013* (2013.01); *G06F 3/04845* (2013.01); *G06F 3/0485* (2013.01); *G06N 20/20* (2019.01); *G06T 7/0012* (2013.01)

(58) Field of Classification Search
None
See application file for complete search history.

(56) References Cited

U.S. PATENT DOCUMENTS

| | | | |
|---|---|---|---|
| 8,954,884 B1 * | 2/2015 | Barger | G06F 3/04817 715/792 |
| 9,289,183 B2 * | 3/2016 | Karssemeijer | A61B 6/502 |
| 11,341,643 B1 * | 5/2022 | Douglas | G09G 5/34 |
| 2009/0028403 A1 * | 1/2009 | Bar-Aviv | G06T 7/0012 382/128 |
| 2021/0345865 A1 * | 11/2021 | Spillinger | A61B 1/041 |
| 2023/0298306 A1 * | 9/2023 | Baras | G06V 10/74 382/128 |

FOREIGN PATENT DOCUMENTS

CN 112651960 A * 4/2021 ............ G06T 7/00

* cited by examiner

*Primary Examiner* — James A Thompson

(57) ABSTRACT

This patent includes techniques for improved rates of display of images within an image set. This is particularly useful to scrolling through medical images. For example, the top of the head on an axial head CT image is a smaller size on the screen as compared to the middle of the head. This patent provides a method for image analysis and medical history analysis to optimize scrolling rates.

20 Claims, 20 Drawing Sheets

| Compression technique | Liver | Lung | Pancreas |
|---|---|---|---|
| FFT | low number of frequencies | higher number of frequencies | higher still number of frequencies |
| JPEG | large x,y boxes, low standard deviation (SD) | smaller x,y boxex, and more boxes, higher SD | still smaller boxes, and more boxes, still higher SD |
| Kolmogorov complexity | large strings of near repetitive data | shorter strings of repetitive data | significantly shorter strings of repetitive data |

Figure 3

Example fixation location, t = j

Example fixation location, t = j+1

Example fixation location, t = k

Example fixation location, t = k+1

Example fixation location, t = *l*

Example fixation location, t = *l*+1

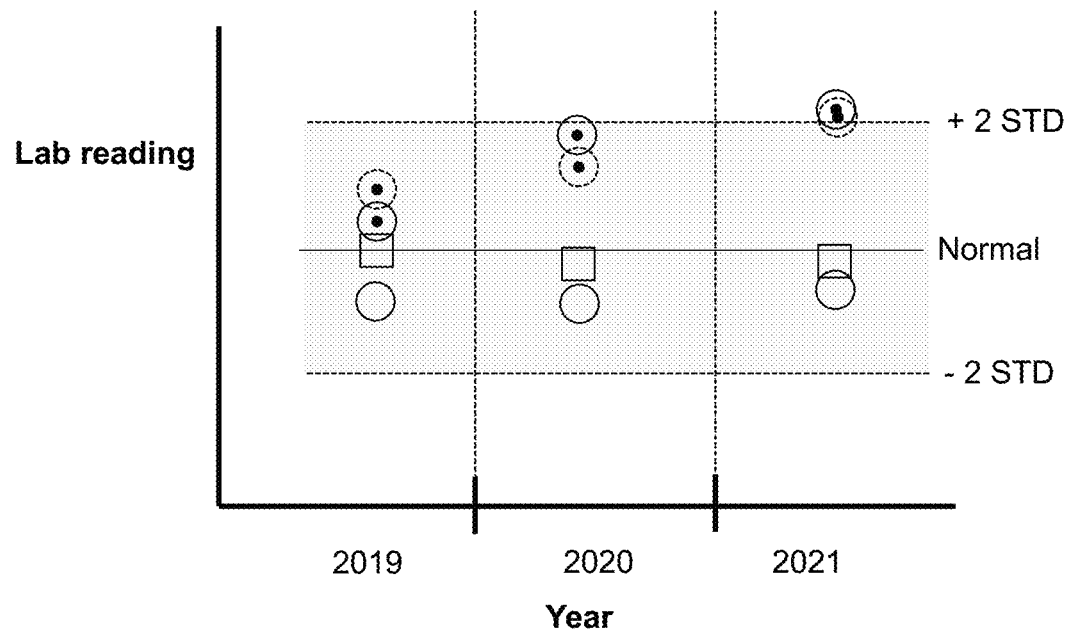
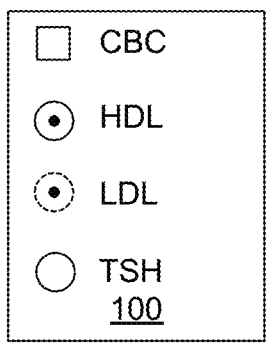
Figure 7

Data plot of x, y, z locations of microcalcifications in breasts.
Long vector projecting down from z-axis away from y-axis toward x-axis indicates possibility of tree like structure – possibly impending cancer – slow scroll rate
1300

Data plot of x, y, z locations of microcalcifications in breasts.
There is no long vector; this favors benignity
1301

USING COMPLEXITY LEVEL TO OPTIMIZE TIME SPENT PER IMAGE

APPLICATION OF ANNs
Fig. 17A ANN Pattern recognition of spiculated tumor tissue
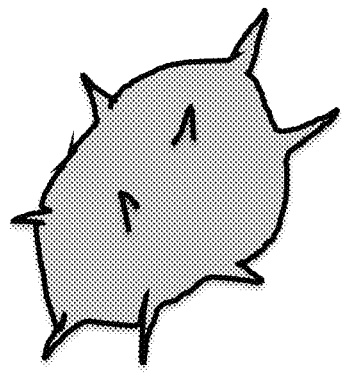
Fig. 17B ANN Pattern recognition of lobulated tumor tissue
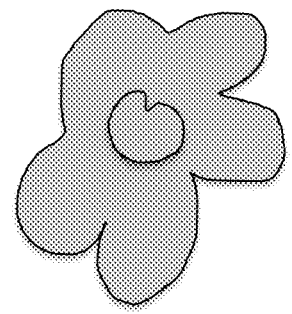

EXAMPLES OF IMAGES WITH SMALL AND LARGE PATIENT DATA

FACTORS IN DETERMINING TIME SPENT PER IMAGE

- Complexity of image
- Size of image
- Probability of image containing pathology
- Shape of structures within image
- Whether structures displayed on images contained pathology on a previous medical imaging examination
- Whether structures displayed on images are correlated to laboratory abnormalities
- Whether structures displayed on images are correlated to physical examination abnormalities
- Whether structures displayed on images are correlated to pharmacotherapy
- Whether structures displayed on images are correlated to an abnormality identified by an artificial intelligence algorithm or a computer aided detection algorithm
- Whether structures displayed on images in said image set are correlated to a diagnosis
- Eye tracking metrics
- A checklist item
- Characterizing a structure by performing at least one of the group consisting of: Naive Bayes; Support Vector Machine; K-nearest neighbors; K-means clusters; principal component analysis; artificial neural networks; linear regression; logistic regression; linear discriminant analysis; and decision tree analysis
- An orientation of a structure
- A spatial relationship between at least 2 segmented structures
- A relationship between consecutively displayed images.

Figure 19

METHOD AND APPARATUS OF UTILIZING ARTIFICIAL INTELLIGENCE IN THE SCROLLING PROCESS

CROSS REFERENCES TO RELATED APPLICATIONS

This patent application is a continuation in part of U.S. Ser. No. 17/230,959 filed on Apr. 14, 2021, which is a continuation in part of U.S. Ser. No. 16/842,631 filed on Apr. 7, 2020, which is a continuation in part of U.S. Ser. No. 16/594,139 filed on Oct. 7, 2019, which claims the benefit of 62/743,837 filed on Oct. 10, 2018. U.S. patent application Ser. No. 17/230,959 also claims the benefit of U.S. Provisional Application No. 63/009,997 filed on Apr. 14, 2020. This patent application is a continuation in part of U.S. Ser. No. 17/340,023 filed on Jun. 6, 2021, which is a continuation-in-part of U.S. patent application Ser. No. 16/752,691 filed on Jan. 26, 2020. All of these related applications are incorporated by reference.

TECHNICAL FIELD

This patent application applies to the field of image analysis.

BACKGROUND

The field of image analysis is growing rapidly in medicine, military, video games and many other industries. Radiologists are commonly concerned.

SUMMARY

All examples, aspects and features mentioned in this document can be combined in any technically possible way.

This patent provides methods, software and hardware for improving the scrolling process. Any user could utilize this process, but the intended user is a radiologist. A CT scan can have hundreds or thousands of slices. This patent improves on the current art by optimizing the amount of time spent on each individual slice.

In the preferred embodiment, an analysis of an image set is performed. The intended use is medical images, so the image set would medical imaging examination, which include but is not limited to the following: computed tomography (CT) scans; magnetic resonance imaging (MRI) scans; ultrasound scans; positron emission tomography (PET) scans; single photon emission computed tomography (SPECT) scans; radiographs; mammograms; digital breast tomosynthesis (DBT) scans; and, scintigraphy scans. A variety of analysis techniques are performed. Images are then displayed in accordance with their assigned amount of time.

First, a complexity assessment for each image in the set of images is performed. For images in said image set. Specifically, the amounts of time to display images within said image set is determined and is based on at least an assigned complexity level. For example, assume a first image is assigned a lower level of complexity than a second image. Assume that the first image is displayed for a first amount of time. Assume that the second image is displayed for a second amount of time. The first image is displayed for a shorter amount of time as compared to said second image.

Second, a size determination for structures displayed on images in said image set is analyzed. Specifically, the amount of time to display images within said image set is based on at least sizes of structures displayed on an image. Assume that a structure displayed is a first size on a first image. Assume that the structure displayed is a second size on a second image. Assume that the first size is smaller than said second size. The first image is displayed for a first amount of time and the second structure is displayed for second amount of time. It should be note that the first image is displayed for a shorter amount of time as compared to said second image.

Third, a probability that an image contains at least one pathology for structures displayed on images in said image set is analyzed. Specifically, the amount of time to display images within said image set is based on at least probabilities of containing at least one pathology for structures displayed on an image. Assume that a first structure has first probability of containing at least one pathology on a first image. Assume that a second structure has second probability of containing at least one pathology on a second image. Assume that the second probability is higher than said first probability. The first image is displayed for a first amount of time and the second structure is displayed for second amount of time. The first image is displayed for a shorter amount of time as compared to said second image.

In addition to these analytical techniques, a variety of additional techniques are also utilized. Some embodiments comprise wherein the analysis comprises determining shapes of structures displayed on images in said image set. Some embodiments comprise wherein the analysis comprises determining whether structures displayed on images in said image set contained pathology on a previous medical imaging examination. Some embodiments comprise wherein the analysis comprises determining whether structures displayed on images in said image set are correlated to laboratory abnormalities. Some embodiments comprise wherein the analysis comprises determining whether structures displayed on images in said image set are correlated to physical examination abnormalities. Some embodiments comprise wherein the analysis comprises determining whether structures displayed on images in said image set are correlated to pharmacotherapy. Some embodiments comprise wherein the analysis comprises determining whether structures displayed on images in said image set are correlated to an abnormality identified by an artificial intelligence algorithm or a computer aided detection algorithm. Some embodiments comprise wherein the analysis comprises determining whether structures displayed on images in said image set are correlated to a diagnosis. Some embodiments comprise wherein the analysis comprises determining eye tracking metrics. Some embodiments comprise using determined amounts of time to display images within said image set to control scrolling rate. Some embodiments comprise using determined amounts of time to display images within said image set to optimize scrolling rate of image slices. Some embodiments comprise using determined amounts of time to display images within said image set to optimize rotation rate for volume rendered images. Some embodiments comprise wherein the analysis comprises determining checklist item. Some embodiments comprise wherein the analysis characterizing a structure by performing at least one of the group consisting of: Naive Bayes; Support Vector Machine; K-nearest neighbors; K-means clusters; principal component analysis; artificial neural networks; linear regression; logistic regression; linear discriminant analysis; and decision tree analysis. Some embodiments comprise wherein the analysis comprises characterizing an orientation of a structure. Some embodiments comprise wherein the analysis comprises characterizing a spatial relationship between at least 2 segmented structures. Some embodiments comprise wherein the analysis comprises characterizing a relationship between consecutively displayed images.

In some embodiments, machine learning algorithms could be leveraged in conjunction with the smart scrolling process which include at least one of the following: supervised machine learning algorithms; unsupervised machine learning algorithms; and reinforcement machine learning algorithms. As an embodiment of supervised machine learning, the attending physician could instruct a radiology resident on initial scrolling rates by type of organ being examined and the needed eye fixation points required for specific organs. For example, the pancreas is complex and can harbor multiple maladies. Such an organ would require, say, 30 such eye fixation points and the associated smart scrolling rate could be one image slice per 9.0 seconds. At this rate, the false negative rate would be low and the probability of a correct diagnosis could be high. In some embodiments, the body organ is less complex (e.g., liver) and require fewer eye fixation points in which case the smart scrolling rate could be one slice per 3.0 seconds. In some embodiments, a receiver operating curve (ROC) could be employed wherein the radiologist probability of correct diagnosis could be constructed as a function of duration of pause during which succeeding image slices are presented. As the radiology resident improved the probability of correct diagnosis, the smart scrolling pause duration could be reduced. In some embodiments, medical care institutions could employ the ROC curve to the radiologist staff in conjunction with gold standard readers to establish credentials of the radiologists.

In some embodiments, the complexity of the scene of the image slice being displayed will, as determined through artificial intelligence, be tied to the smart scrolling process. The scene complexity will be inversely correlated with the automatic scrolling rate. Specifically, the automatic scrolling rate would be slower for medical images with higher complexity and faster for images with lower complexity. Measures of complexity of an image slice or of a region of interest such as a body organ can be obtained by mathematical techniques/programs such as, but not limited to, Fast Fourier Transform (FFT), Joint Photographic Experts Group (JPEG), Kolmogorov complexity, calculating mean and standard deviation.

In some embodiments, supervised machine learning algorithms will be leveraged with the smart scrolling process in a category of regression include but are not limited to: linear regression; logistics regression; and decision trees to include random forests. In some embodiments, the linear regression will use scene complexity to determine or read out the scrolling rate. In some embodiments, logistics regression could be employed. An example embodiment might be for display of the patient's laboratory values. Further, laboratory results from previous tests taken over time could all be plotted on the same logistics regression chart to provide a patient's laboratory history at a glance and reduce scrolling through multiple records. In some embodiments, decision trees could be employed. An example embodiment would be regarding whether a previous set of images had been taken and were part of the patient's records. Given an affirmative answer, this image set(s) could be retrieved and displayed alongside of the current set. In some embodiments, random forests could be employed inter alia to examine a patient's medications in conjunction with the patient's laboratory results to determine changes to dosages, if necessary. This embodiment example of implementation of random forests would reduce scrolling through patient's records and going back and forth between laboratory results and medication lists. X-axis: scene complexity measure (as determined by e.g. JPEG) y-axis: pause per image frame.

In some embodiments, supervised ML algorithms related to the smart scrolling process in the category of classification include but are not limited to: naïve Bayes; support vector machine; and K-nearest neighbor type algorithms. In some embodiments, the naive Bayes could, inter alia, be utilized to classify tissue types in conjunction with medical facility check list for radiologists to segment and filter the image slices and present only pixel (or voxels) which contain tissue for the particular check list item at hand. This would, in turn, reduce the number of eye fixation points presented on the display and scroll rate could increase accordingly. Specifically, in this embodiment, the eye would not be drawn to pixels/points external to the checklist item at hand since, through the segmentation and filtration process, the pixels external to the checklist item at hand would not be displayed. As a consequence, these external potential eye fixation would not be displayed and the scrolling process speeded up correspondingly. In some embodiments, the support vector machine (SVM) could, inter alia, be utilized to create hyper planes between different types organs/tissue. This SVM algorithm, in conjunction with medical facility check list for radiologists, be utilized to segment and subsequently filter the image slices and present only pixel (or voxels) which contain tissue for the particular check list item at hand. This would, in turn, reduce the number of eye fixation points presented on the display and scroll rate could increase accordingly. In some embodiments, the K-nearest neighbor (KNN) type algorithm could, inter alia, be utilized to classify tissue types. This KNN algorithm, in conjunction with medical facility check list for radiologists, be utilized to segment and subsequently filter the image slices and present only pixel (or voxels) which contain tissue for the particular check list item at hand. This would, in turn, reduce the number of eye fixation points presented on the display and scroll rate could increase accordingly. Additional techniques applied include those described in U.S. Pat. No. 10,586,400 Processing 3D medical images to enhance visualization.

In some embodiments, unsupervised machine learning algorithms associated with dimensionality reduction could be utilized in conjunction with smart scrolling include but, are not limited to: principal component analysis and linear discriminant analysis. Principal component analysis (PCA) could be important in early detection of breast cancer in identifying the structure of micro calcifications within the breast. In some embodiments, segmentation and filtering may be employed to remove non-micro calcification tissue from the display and PCA then be applied. A tree like structure of the micro calcifications would be indicative of potential impending cancer, whereas, a random pattern of the micro calcifications would not be of concern. A strong/long PCA principal vector suggests a tree-like structure whereas, multiple PCA vectors of approximately the same strength/length suggest a random pattern. In this embodiment, knowledge of the a strong/longer principal coupled with the direction of the vector will significantly assist in smart scrolling to properly connect the micro calcification dots and verify if, in fact, a structure indicative of cancer is present. Further, in this embodiment, knowledge of multiple PCA vectors of approximately similar strength/length will significantly assist in smart scrolling to verify if, in fact, a random structure indicative of a benign condition.

In some embodiments, linear discriminant analysis could be employed, for example, when two factors affect scrolling rate. For example, type of organ being examined (e.g., liver vs. pancreas) and complexity of the image slices of that organ.

In some embodiments, unsupervised machine learning algorithms associated with clustering could be utilized in conjunction with smart scrolling include but, are not limited to: K-means and K-mediods. Clustering algorithms may detect groupings of tumorous tissues in which case the smart scrolling could rapidly move to the slice(s) or voxel(s) to expedite the radiologist review. For example, in K-means the smart scrolling could go directly to the centroid of the cluster. If combined with segmentation and filtering, accurate staging of the tumor would be facilitated. In some embodiments, the probability of anomaly detection can be facilitated through cluster analysis in which case the smart scrolling could rapidly move to the slice(s) or voxel(s) to expedite the radiologist review. In this embodiment, cluster analysis-based outlier detection could signal smart scrolling to the outlier location slice(s) for inspection by the radiologist.

In some embodiments, artificial neural network (ANN) will be utilized in conjunction with smart scrolling. An example would be in investigating whether a breast tumor was smooth or speculated wherein ANN pattern analysis could be applied and the smart scrolling rapidly move to the area/volume of concern. Another example wherein pattern analysis capability of ANN could be of utility is in discerning the structure of micro calcifications within the breast and smart scrolling moving rapidly to the image(s)/volume for radiologist review.

In some embodiments, the physical size of the of the area which contains pixels/voxels of patient imagery within the slice could be correlated with the pause duration during smart scrolling—the larger the area, the longer the pause. And correspondingly, the smaller the area, the shorter the pause.

In some embodiments, multiple artificial intelligence algorithms can be combined and then smart scrolling applied. An example would be K-means algorithm applied to a set of medical images to identify if a cluster of potentially tumorous tissue is present and, if so, then apply Artificial Neural Net applied to examine the shape/pattern of the cluster. In this embodiment, the smart scrolling could proceed directly to the cluster for the radiologist confirmation of type of tissue mass.

In some embodiments, a Praeto analysis can be performed. In some embodiments, a machine learning algorithm can be used to determine an auto scroll rate. Some embodiments comprise wherein the analysis is based on number of fixation points (as determined by an eye tracking system). Some embodiments comprise wherein the complexity of the image is determined by: FFT; JPEG; Kolmogorov complexity; and, compete mean and standard deviation. Some embodiments comprise wherein the analysis includes a differential diagnosis, a priority of diseases. Some embodiments comprise wherein natural language processing/speech recognition is utilized.

Some of the techniques in this patent are performed in conjunction with techniques disclosed in the following patents (all of which are incorporated by reference in their entirety): U.S. patent application Ser. No. 15/878,463, Interactive 3D cursor for use in medical imaging; U.S. patent application Ser. No. 16/010,925, Interactive placement of a 3D digital representation of a surgical device or anatomic feature into a 3D radiologic image for pre-operative planning; U.S. patent application Ser. No. 15/904,092, Processing 3D medical images to enhance visualization; U.S. patent application Ser. No. 15/949,202, Smart operating room equipped with smart surgical devices; U.S. Pat. No. 9,473,766, Method and apparatus for three dimensional viewing of images; U.S. Pat. No. 9,615,806, Method and apparatus for creation and display of artifact corrected three dimensional (3D) volumetric data from biplane fluoroscopic image acquisition; U.S. patent Ser. No. 14/644,489, Method and apparatus for creation and display of artifact corrected three dimensional (3D) volumetric data from biplane fluoroscopic image acquisition; U.S. Pat. No. 9,980,691, Method and apparatus for three dimensional viewing of images; U.S. Pat. No. 9,349,183, Method and apparatus for three dimensional viewing of images; U.S. patent application Ser. No. 16/195,251, Interactive voxel manipulation in volumetric medical imaging for virtual motion, deformable tissue, and virtual radiological dissection; U.S. patent application Ser. No. 16/509,592, Implantable markers to aid surgical operations; U.S. patent application Ser. No. 16/524,275, Using geo-registered tools to manipulate three-dimensional medical images; PCT/US19/478, A virtual tool kit for radiologists; U.S. patent application Ser. No. 16/563,985, A method and apparatus for the interaction of virtual tools and geo-registered tools; U.S. patent application Ser. No. 16/594,139, Method and apparatus for performing 3D imaging examinations of a structure under different configurations and analyzing morphologic changes; U.S. patent application Ser. No. 16/683,256, Method and apparatus for performing 3D imaging examinations of a structure under different configurations and analyzing morphologic changes; U.S. patent application Ser. No. 16/703,629, Radiologist-assisted machine learning with volume-subtending 3D cursor; PCT/US19/239, Radiologist-assisted machine learning with interactive, volume-subtending 3D cursor; U.S. provisional application No. 62/843,612, A method of creating a computer-generated patient specific image; U.S. provisional application No. 62/846,770, A method of prioritized volume rendering to improve visualization of prioritized items within a 3D volume; U.S. provisional application No. 62/850,002, A method of creating an artificial intelligence generated differential diagnosis and management recommendation tool boxes during medical personnel analysis and reporting; U.S. patent application Ser. No. 16/654,047, A method to modify imaging protocols in real time through implementation of artificial intelligence; U.S. provisional application No. 62/856,185, A method of image manipulation based on eye tracking; U.S. patent application Ser. No. 16/506,073, A method for illustrating direction of blood flow via pointers; U.S. patent application No. 62/906,125, A method and apparatus for stereoscopic rendering of mobile fluids; and, U.S. patent application No. 62/939,685, Method and apparatus for development of an organ-specific coordinate system.

BRIEF DESCRIPTION OF FIGURES

FIG. 3 illustrates a table of statistics of slice complexity.

FIG. 7 illustrates plotting lab values on a single visual chart.

FIG. 13B illustrates an example graph with vectors derived from Principal Component Analysis (PCA) of the structure of breast micro calcifications of a cluster-like.

FIG. 17A illustrates an example Artificial Neural Networks (ANN) applied to breast tumors.

FIG. 17B illustrates an example Artificial Neural Networks (ANN) applied to breast tumors.

FIG. 19 illustrates factors in determining the amount of time spent per image.

DETAILED DESCRIPTION OF FIGURES

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

Figure 1A:
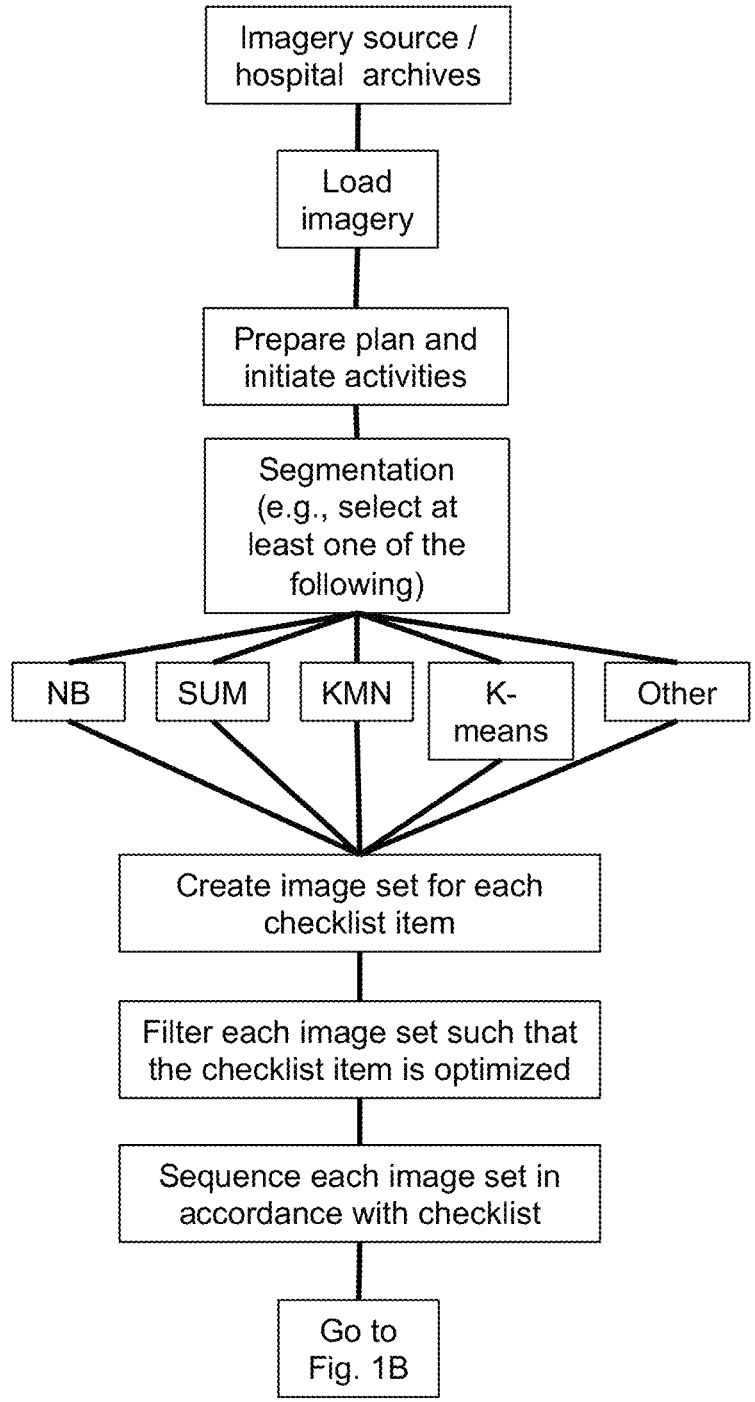
FIG. 1A illustrates part 1 of flow chart process.

FIG. 1A illustrates part 1 of flow chart process. Part 1 of the Flow Chart sets up the review process for a set of medical imagery by a radiologist. A basis for the process is the hospital or medical facility policies and procedures. These may include but are not limited to: review checklist sequence; emergency review/actions; handling of patient's records; reporting procedures, etc. The first active step of the radiologist would be to download the set of imagery; associated patient's records; any laboratory results; receiving physicians' notations regarding patient's condition and other relevant information. At this juncture, the radiologist review plan would be prepared and initial activities commenced. One of the critical steps is segmentation in accordance with the hospital checklist. This is important because during each checklist item review, only the particular checklist organ/body structure will be presented for scrolling through. Alternatively, the checklist item could be optimized (e.g., via windowing and leveling or via the "double windowing" technique taught in U.S. Pat. No. 10,586,400). This removes distractions from view and focuses the radiologist's attention. A number of analytical techniques are available for segmentation. These include, but are not limited to the following: Naïve Bayes (NB); Support Vector Machines (SVM); K-Nearest Neighbor (KNN); and other segmentation processes. The next step would be to create a unique image set for each checklist item. This would be followed by a filtration process, which would remove all of the tissue surrounding the checklist item or present the checklist item in an optimized fashion, as previously discussed. Next comes the sequencing of these filtered (or optimized, as previously discussed) image sets in accordance with the hospital checklist-Part 2.

Figure 1B:
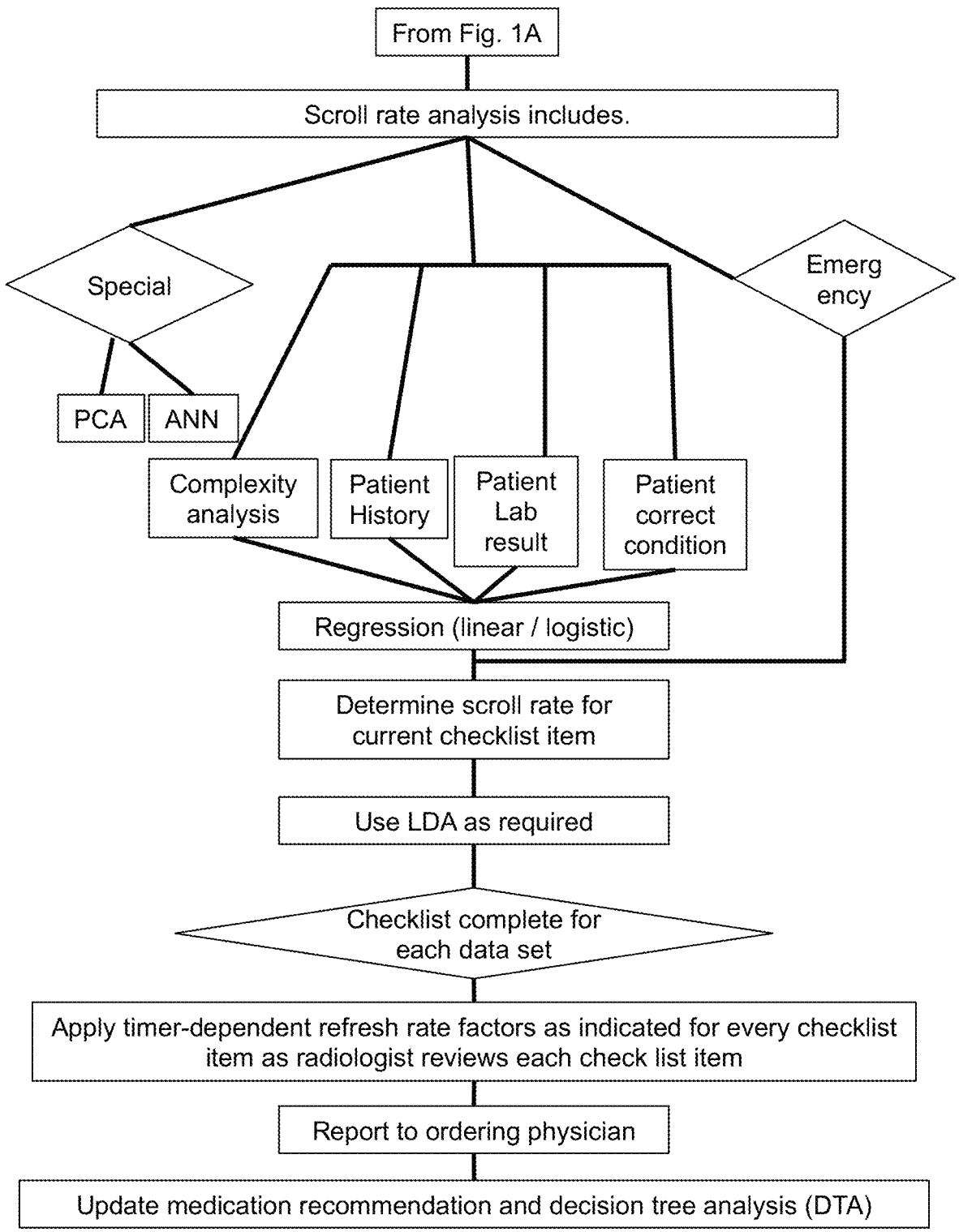
FIG. 1B illustrates part 2 of flow chart process.

FIG. 1B illustrates part 2 of flow chart process. Part 2 of flow chart process how one would arrive at the scroll rate analysis and associated actions. It should be noted that the process is performed in an iterative manner starting with the first item in the checklist and on through the list. Going from right to left. Analysis of the scroll rate would first check if emergency conditions applied. Is so, the plan would be truncated and the radiologist notified of the emergency condition and relevant image set(s) brought to the first to be reviewed. Next, the majority of the image sets would undergo analytical procedures to couple the scroll rate with existing patient condition in an optimal manner (described in more detail in subsequent figures). These analytical procedures would include, but not be limited to the following. The first procedure would be analysis of complexity of each individual image. This would include a linear regression that quantifies scroll rate with degree in image complexity. Next, if patient's history were available and applicable to the checklist item at hand, a logistics type regression would be performed. Next, if patient's laboratory results were available and applicable to the checklist item at hand, a logistics type regression would be performed. Next, if notes pertaining to patient's condition at time of hospital admission (or requesting physician order for imaging) were available and applicable to the checklist item at hand, a logistics type regression would be performed. Next, two special types of analysis would be performed. First, a principle component analysis (PCA) to determine of there was a tell tale structure of micro calcifications (perhaps indicating a pre-cancerous condition). Next, artificial neural networks (ANN) would be performed for any tumorous tissue (again indicating a pre-cancerous/cancerous condition). These techniques could be performed for breast imaging. The next step would be to combine all of the above into a scroll rate for the checklist organ/structure at hand. This would include performing a linear discriminant analysis (LDA), as required. Then, the iteration takes place to the next item on the checklist. When all checklist items have been reviewed, the report would be prepared for the proscribing physician. As a note, recommendation regarding level of medication could be made based on decision tree analysis (DTA).

Figure 2A:
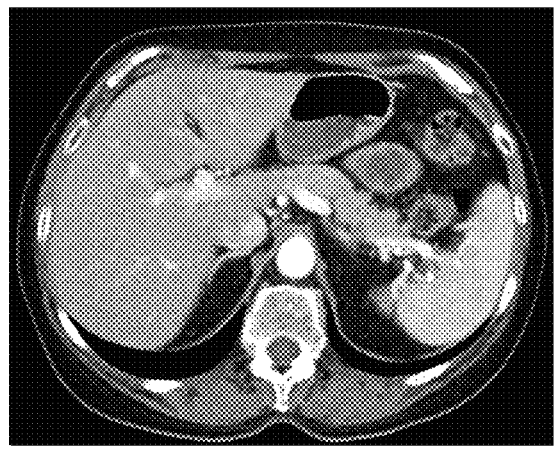
FIG. 2A illustrates an example slice of pancreas, which presented with high complexity.

FIG. 2A illustrates an example slice of pancreas, which presented with high complexity. Three examples are provided wherein differing levels of complexity of scenes within image slices are provided. In complex images, it is difficult to detect anomalous tissue that blends in the adjacent pixels/voxels. Further, due to the degree of complexity, the eye is drawn to a corresponding number of eye fixation points. If sufficient time is not allocated during the scrolling process to cover the eye fixation points required due to the complexity of the image, the probability of correct diagnosis is reduced. The radiologists can compensate for this phenomenon by increasing the time that he/she spends on each slice. In FIG. 2A, a slice of a pancreas is shown. This illustrates a complex slice wherein the radiologist must carefully examine many distinct areas, which could potentially harbor serious diseases. Under this patent, the artificial intelligence aspect applied to the slices to determine complexity and the smart scrolling process would leverage this inter-relationship and increase the automatic pause duration when slices with high complexity of scenes were displayed to the radiologist.

Figure 2B:
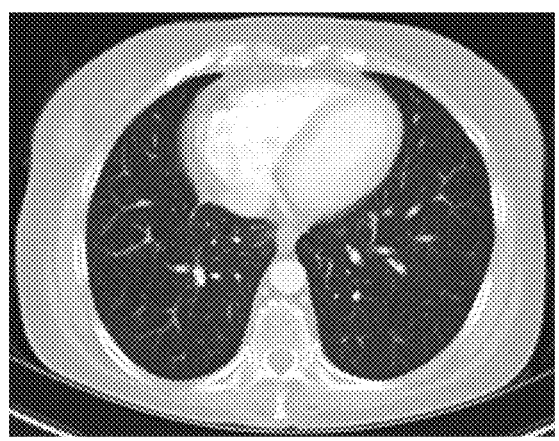
FIG. 2B illustrates an example slice of lung, which presented with moderate complexity.

FIG. 2B illustrates an example slice of lung, which presented with moderate complexity. The complexity of scenes of a lung displayed in FIG. 2B are less than those of the pancreas. Eye fixation points are fewer and anomalous tissue (e.g., tumor) stands out with respect to adjacent, non-tumorous tissue. Radiologist required review time is thereby reduced. Under this patent, the artificial intelligence aspect applied to the complexity of slices would leverage this inter-relationship and moderate the automatic pause duration when slices with medium complexity of scenes were displayed to the radiologist.

Figure 2C:
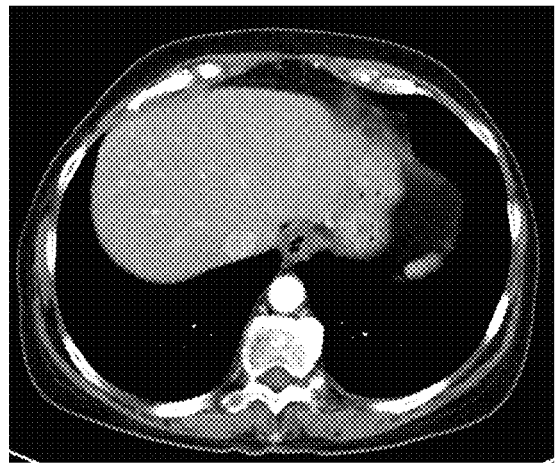
FIG. 2C illustrates an example slice of liver, which presented with low complexity.

FIG. 2C illustrates an example slice of liver, which presented with low complexity. The tissue of the liver is of fairly uniform/homogenous density and, therefore, a normal liver can be reviewed in a fairly rapid manner without the concern of missing a key element in correct diagnosis. Due to the fairly uniform/homogenous density of the tissue eye fixation points are fewer and anomalous tissue (e.g., tumor) stands out with respect to adjacent, non-tumorous tissue. Under this patent, the artificial intelligence aspect applied to the slices would leverage this inter-relationship and reduce the automatic pause duration when slices with low complexity of scenes were displayed to the radiologist.

FIG. 3 illustrates a table of statistics of slice complexity. There are multiple ways to measure scene complexity within an image slice. These include but, are not limited to: Fast Fourier Transform (FFT), Joint Photographic Experts Group (JPEG), Kolmogorov complexity, calculating mean and standard deviation. The FFT represents the image in the frequency domain—selecting some frequencies and rejecting others. A low number of frequencies would be representative of a less complex image. The JPEG determines the degree the image can be compressed—the more it can be compressed, the less complex the image is. An image slice with a low standard deviation is less complex than one with a high standard deviation. A table is provided which presents these statistical measures for each of the figures in FIGS. 2A, 2B and 2C. The statistical measures will provide the basis for quantifying the interrelationship between scene complexity within an image slice and the pause duration during which the image slice is presented on the radiologist display.

Figure 4A:
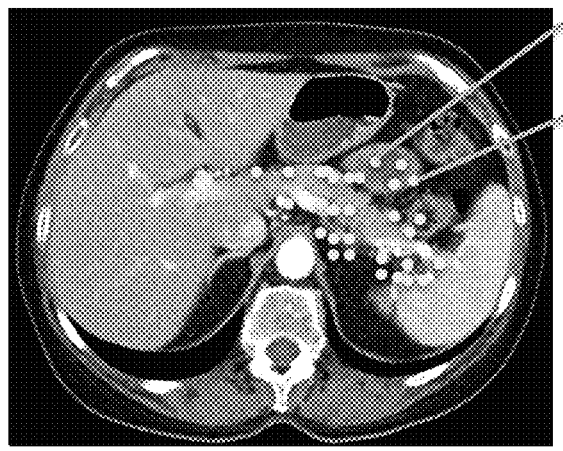
FIG. 4A illustrates example eye fixation points on FIG. 2A.

FIG. 4A illustrates example eye fixation points on FIG. 2A. The purpose of this figure is to illustrate saccadian eye movement on scenes of different complexity of FIG. 2A. During the radiologist review of an image, the radiologist eye jumps from one point to another in a rapid fashion and from this the brain deduces the important elements of the slice. 30 fixation points are illustrated spread out over the pancreas region. A first fixation location is labeled at time=j. A second fixation location is labeled at time=j+1.

Figure 4B:
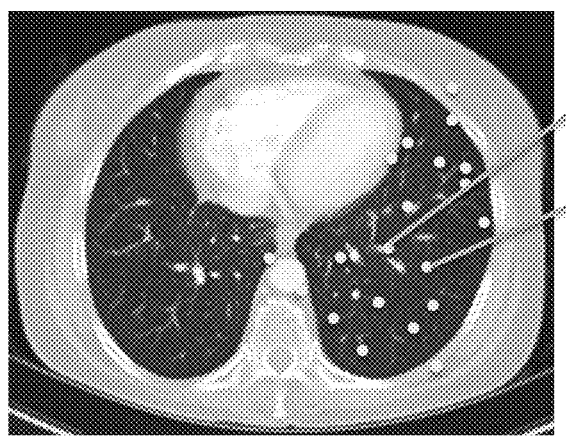
FIG. 4B illustrates example eye fixation points on FIG. 2B.

FIG. 4B illustrates example eye fixation points on FIG. 2B. Approximately 20 fixation points are illustrated spread out over the left lung region. A first fixation location is labeled at time=k. A second fixation location is labeled at time=k+1.

Figure 4C:
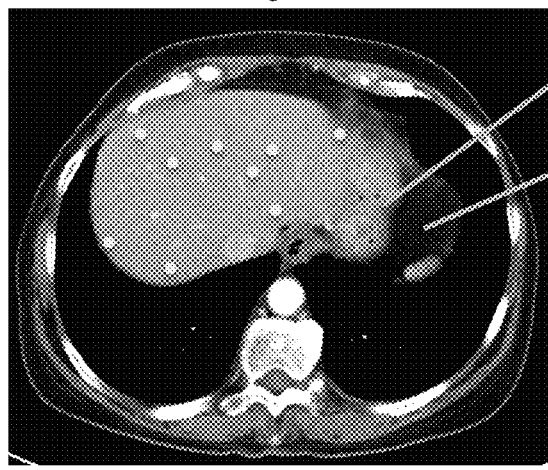
FIG. 4C illustrates example eye fixation points on FIG. 2C.

FIG. 4C illustrates example eye fixation points on FIG. 2C. Approximately 10 fixation points are illustrated spread out over the liver region. A first fixation location is labeled at time=1. A second fixation location is labeled at time=1+1.

Figure 5:
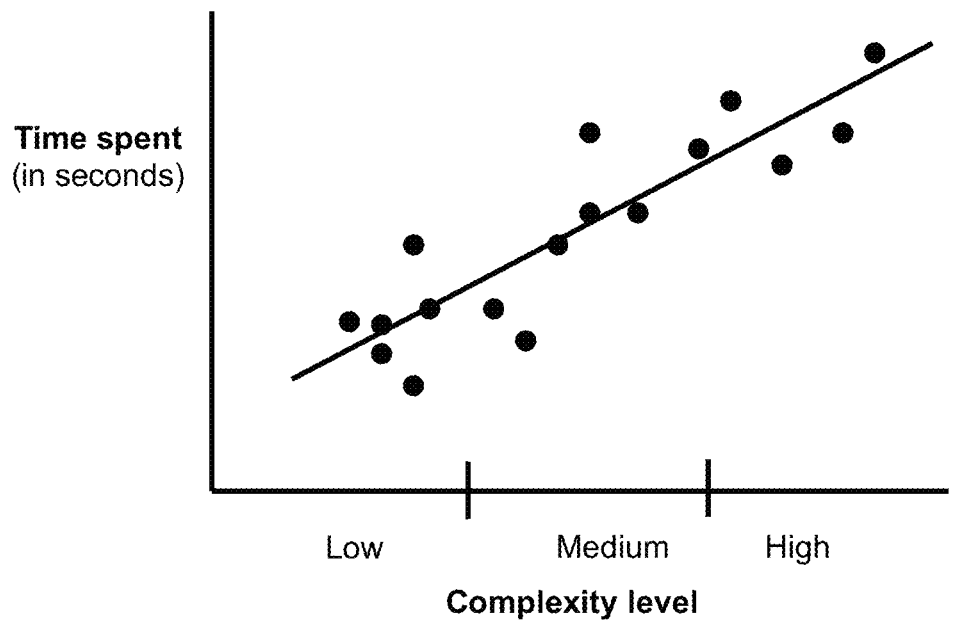
FIG. 5 illustrates using complexity level to optimize time spent per image.

FIG. 5 illustrates using complexity level to optimize time spent per image. Note that each data point represents a fixed level (e.g., 90%) of probability of correct classification. Each data could represent a group of users. This chart provided an example of Linear Regression being applied to quantify the interrelationship between image (e.g., slice) complexity and the duration of the pause for each image (e.g., slice) slice to be presented to the radiologist. Note that then the image complexity is low, the pause if of short duration—reflecting the fewer eye fixation points and, potentially, conspicuity of any anomalous tissue. As the transition goes from low complexity to moderate complexity, the pause increases. Further, when the slice become even more complex, the pause duration further increases.

Figure 6A:
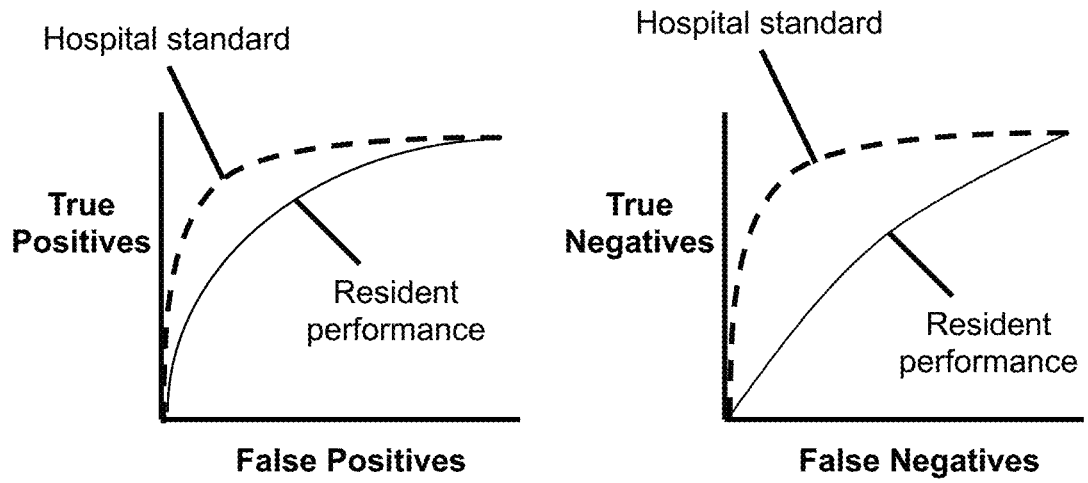
FIG. 6A illustrates an example Receiver Operating Curve (ROC) as applied to Probability of Correct Diagnosis as a function of pause duration.

FIG. 6A illustrates an example Receiver Operating Curve (ROC) as applied to Probability of Correct Diagnosis as a function of pause duration for a resident early in the training. The ROC curve inter relates two important items regarding a particular radiologist (or group of radiologists) performance level: the rate of true positives vs. false positives; and true negative vs. false negatives. It is important for both medical colleges and treatment facilities to quantify the capabilities of the radiologists. From a medical college perspective, there is a need to understand how well the radiologist resident performs in terms of probability of correct diagnosis and, importantly, to track how that performance improves over the residential period. From the medical facility perspective, there is the economic stress between meeting the radiological needs (i.e., reading all of the medical images in a timely manner) time wise (and subject to the limited radiologist staff due to costs) and providing correct diagnoses. This pushes the radiologist to rush through medical images creating stress and leaving open the possibility of missed diagnosis with both proper medical care and legal implications. The question arises 'how fast is too fast' and how slow is sufficient for high probability of correct diagnosis. ROC curves help provide a quantitative measure of the relationship between Probability of Correct Diagnosis ($P_{CD}$) and Pause Duration during which a slice is presented on the radiologist display. ROC curves can track radiologist residents learning progress over time as well as current radiologist performance. The unifying measure on this is the pause time duration during which a slice is presented on the radiologist display. FIG. 6A illustrates an example at time point 1 wherein a resident is at an early point in his/her learning and the resident performance (solid line) is not up to the institution goals (dashed line).

Figure 6B:
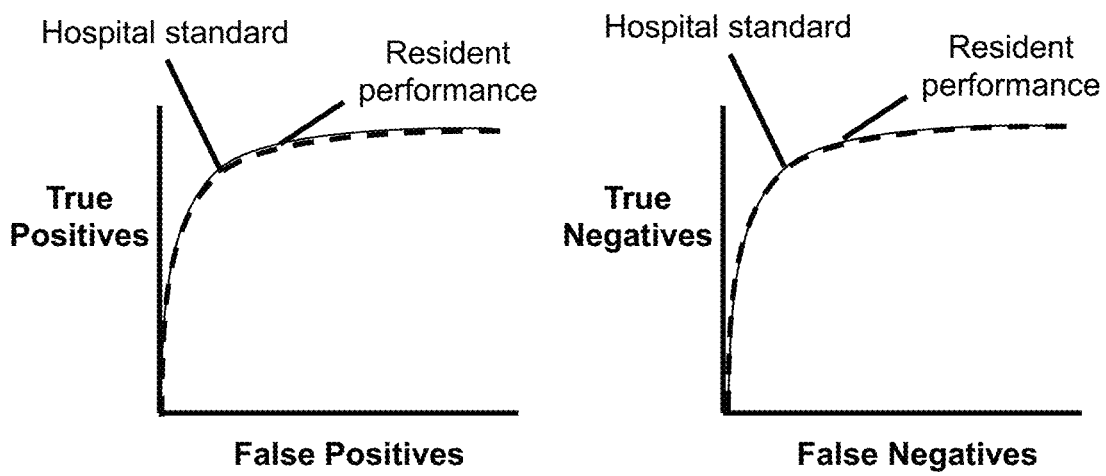
FIG. 6B illustrates an example Receiver Operating Curve (ROC) as applied to Probability of Correct Diagnosis as a function of pause duration for a resident later in training.

FIG. 6B illustrates an example Receiver Operating Curve (ROC) as applied to Probability of Correct Diagnosis as a function of pause duration for a resident later in training. Note that the resident performance (solid line) meets that of the institution goals (dashed line).

FIG. 7 illustrates plotting lab values on a single visual chart. Traditionally, lab values are viewed one at a time. Using current methods, it is difficult to assess all lab values at all times (e.g., multiple years) in a single image. This novel display illustrates a time as the x-axis and the lab reading in the y-axis. All continuous variables are plotted on a single chart with a center horizontal line illustrating the normal (mean) value. Note that in the pediatrics population, each value would be normalized to the patients age at the time the test was acquired. A second horizontal line illustrates 2 SD above the mean. A third horizontal line illustrates 2 SD below the mean. Additional lines could be used for binary or categorical test results, as desired.

Next, an example of Logistics Regression as applied to a patient's medical laboratory results is discussed. The purpose of this figure is to illustrate a one chart method for medical personnel (not only radiologists but, doctors, physician's assistants, nurses, patients/family, others, as necessary) to view medical laboratory results. This is done through a logistics regression chart wherein a line(s) establishes the acceptable level of laboratory result-above (or below) which is out of normal range. Quantitative means could show how far above/below the line these results measured. Color codes for the chart background could be employed (e.g., green background above the line for normal-red below the line for out of range). Note: where multiple levels of conditions were included in the laboratory results, multiple lines could be drawn to reflect degree of patient condition. Alternatively, as illustrated in this figure different symbols could be for different categories of blood tests (e.g., cholesterol levels (HDL/LDL; complete blood count (CBC); thyroid stimulating hormone (TSH). A wide range of medical tests could be placed on this same chart (e.g., sleep study, physical examination, fitness test, radiology exam, cardiology exam, EEG, and many others). Conditions could be plotted over time as illustrated and the patient's current condition compared with previous laboratory tests. This saves in the scrolling time to present multiple pages of laboratory results and gives a complete laboratory picture of patient condition in one readily understandable chart. Logistics Regression could also be applied to a patient's medical laboratory results over multiple time periods. The scrolling back through multiple records to find previous laboratory results, and then the back and forth to make comparisons is obviated-thus saving time and facilitation of correct interpretation of patient condition.

Figure 8A:
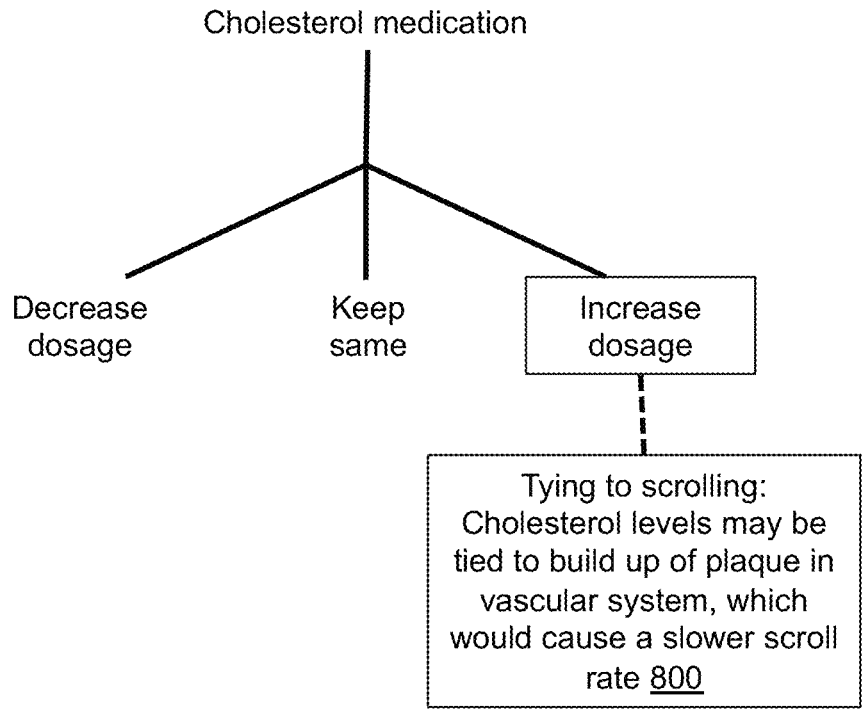
FIG. 8A illustrates an example of random trees mapping out prescription changes, which changed.

FIG. 8A illustrates an example of random trees mapping out prescription changes, which changed. This particular chart shows use of random trees to help visualize the current status of a patient's medications. During an annual physical, the physician would need to scroll through the patient's medical records and try to deduce a correct list of the type medications and dosage from reading doctor's reports' showing what we prescribed and dosage thereof. In this particular figure, this extensive scrolling through medical records is obviated by using each of the Random Forest Trees shows a particular medication type. There are three branches on these inverted trees: increase dosage; decrease dosage; and no change to dosage. Note that the display of the Logistics Regression of laboratory results over time (FIG. 7 in conjunction with the Random Trees thus speeding the process and linking key information to facilitate medical decisions. Note that this can be tied into scrolling: Cholesterol levels may be tied to build up of plaque in vascular system, which would cause a slower scroll rate.

Figure 8B:
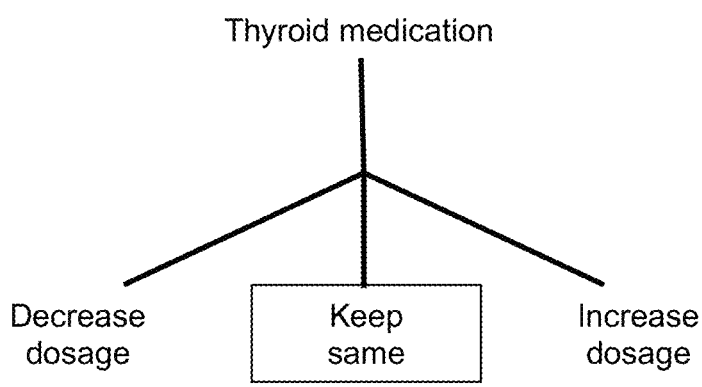
FIG. 8B illustrates an example of random trees mapping out prescription changes, which changed.

FIG. 8B illustrates an example of random trees mapping out prescription changes, which changed.

Figure 9:
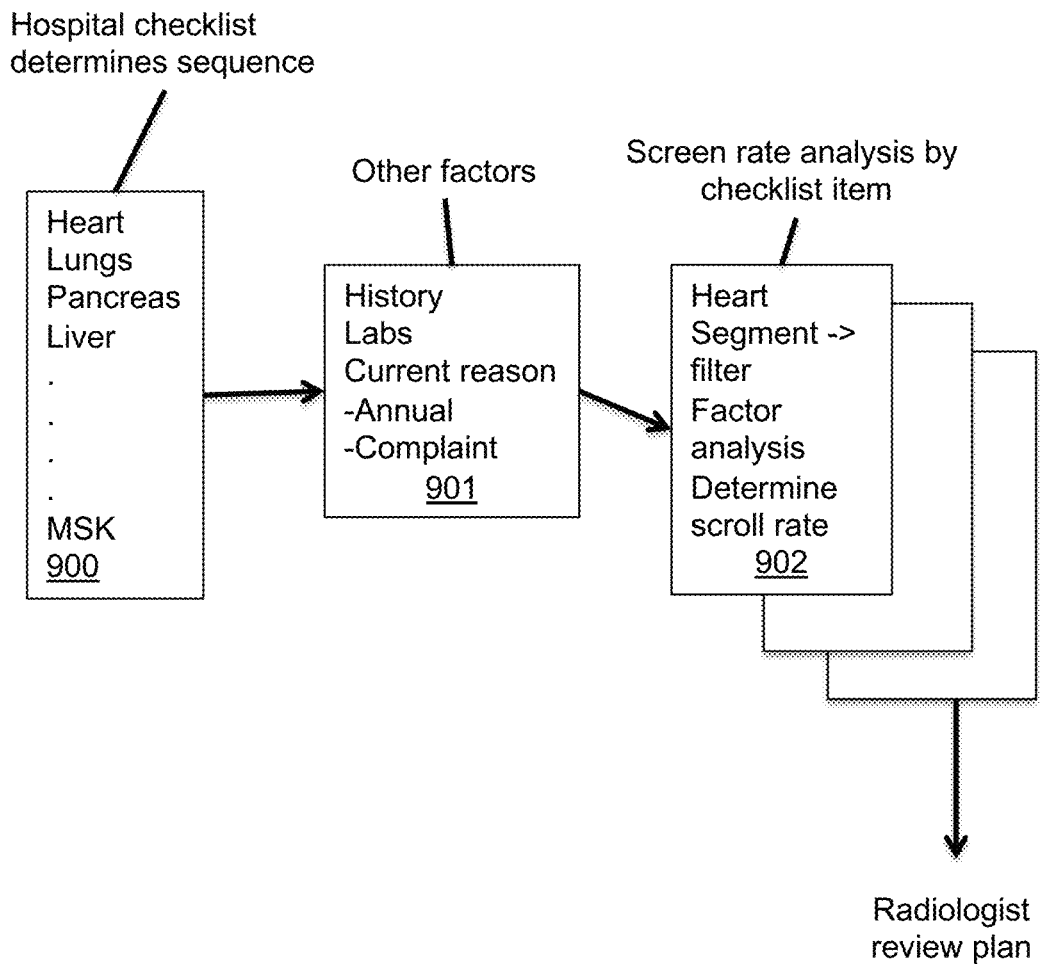
FIG. 9 illustrates an example of a radiologist's review plan.
Figure 10:
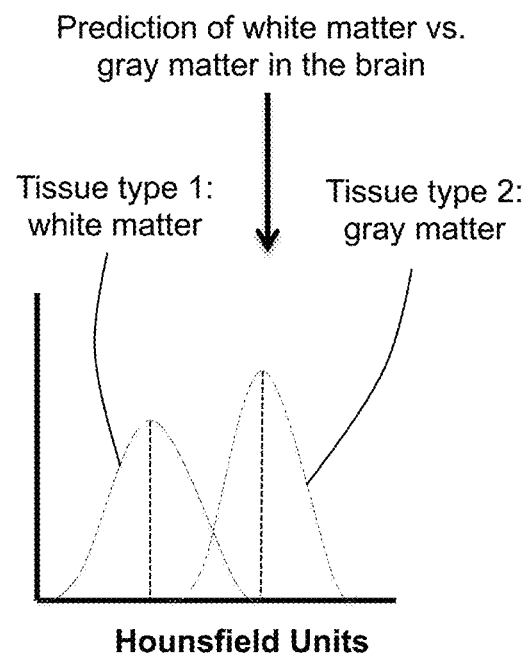
FIG. 10 illustrates using Naïve Bayes for classification of tissue types.

FIG. 9 illustrates an example of a radiologist's review plan. 900 illustrates checklist items. The plan could include the display sequence, composition which could include patient's history, laboratory results, current reason for radiological imaging, and other factors 901. The plan would also include analytical procedures to be applied to image sets in order to determine the optimal pause time duration during which a slice is presented on the radiologist display 902. The could also apply radiologist specific preferences in the display process. The plan would then be turned into actions FIG. 10 illustrates using Naïve Bayes for classification of tissue types. One of the concepts in the Smart Scrolling Patent is that segmentation and filtering will play a key role in speeding the radiologist review process and have an additional benefit in increasing the radiologist probability of correct diagnosis. To repeat, if the segmentation and filtering is linked with the medical facility checklist, then instead of displaying the entire slice, only that data within a slice pertaining to the particular item on the checklist at hand will be displayed. This will eliminate eye fixation points on the slice which are external to the particular item and thus speed the review process. Correct classification of the tissue of the particular item at hand on the checklist is essential and artificial intelligence algorithms offer several means by which correct classification can be accomplished. Three examples in this and following figures are cited but are not limited to the following: Naïve Bayes; Support Vector Machines and K-nearest Neighbor are three such algorithm types. In this particular example, the particular item on the checklist is the head tissue. For illustrative purposes, Naïve Bayes (NB) is applied to the head to determine the boundary between white matter and gray matter for segmentation purposes. Once the is established, those pixels external to the boundary are then filtered (i.e., removed) and the image displayed contains only white matter (or, alternatively, gray matter) pixels (or voxels). In this figure, note that the relative probabilities of white and gray matter are plotted against Hounsfield Units (HU) and white and gray matter have an average of 25 and 35 HUs respectively. Based on these probabilities and applying the NB formula, the respective boundaries can be derived.

Figure 11:
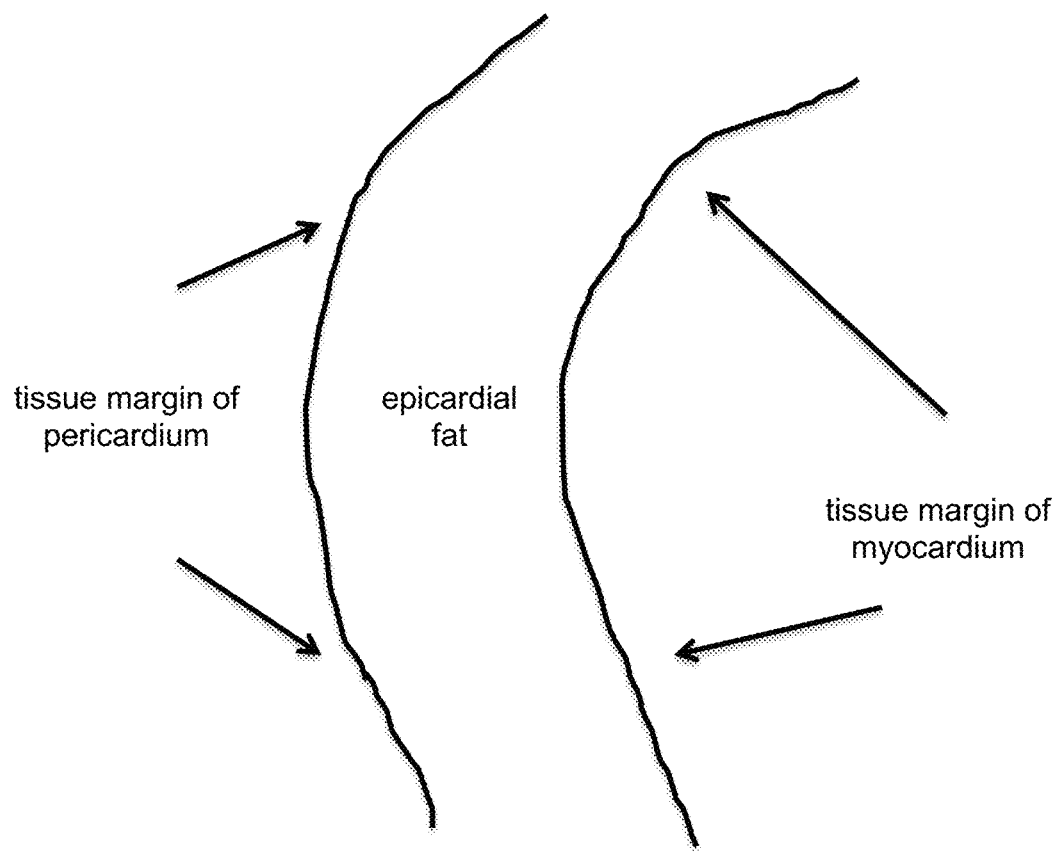
FIG. 11 illustrates using Support Vector Machine preparing hyper planes to separate organs.

FIG. 11 illustrates using Support Vector Machine (SVM) preparing hyper planes to separate organs. In a similar manner to Naïve Bayes, SVM can be utilized in the segmentation process. In this figure a curvilinear hyper plane is illustrated, SVM would generate hyper plane(s) of multiple dimensions so as to (in this figure) encase the heart. A kernel in the SVM process enables the hyper plane to bulge out and enables a better fit with the shape of the heart. The filtering process would be as described in FIG. 10. In this particular example, the goal was to encase the heart through segmentation and then through filtration subtract tissue external to the heart. Collectively, this filtration and segmentation will speed the scrolling process through helping the radiologist focus only on the heart without distraction of having some eye fixation points being eternal to this checklist item of interest. A SVM is used to separate heart from epicardial fat. The filtering process would be as described in FIG. 10.

Figure 12:
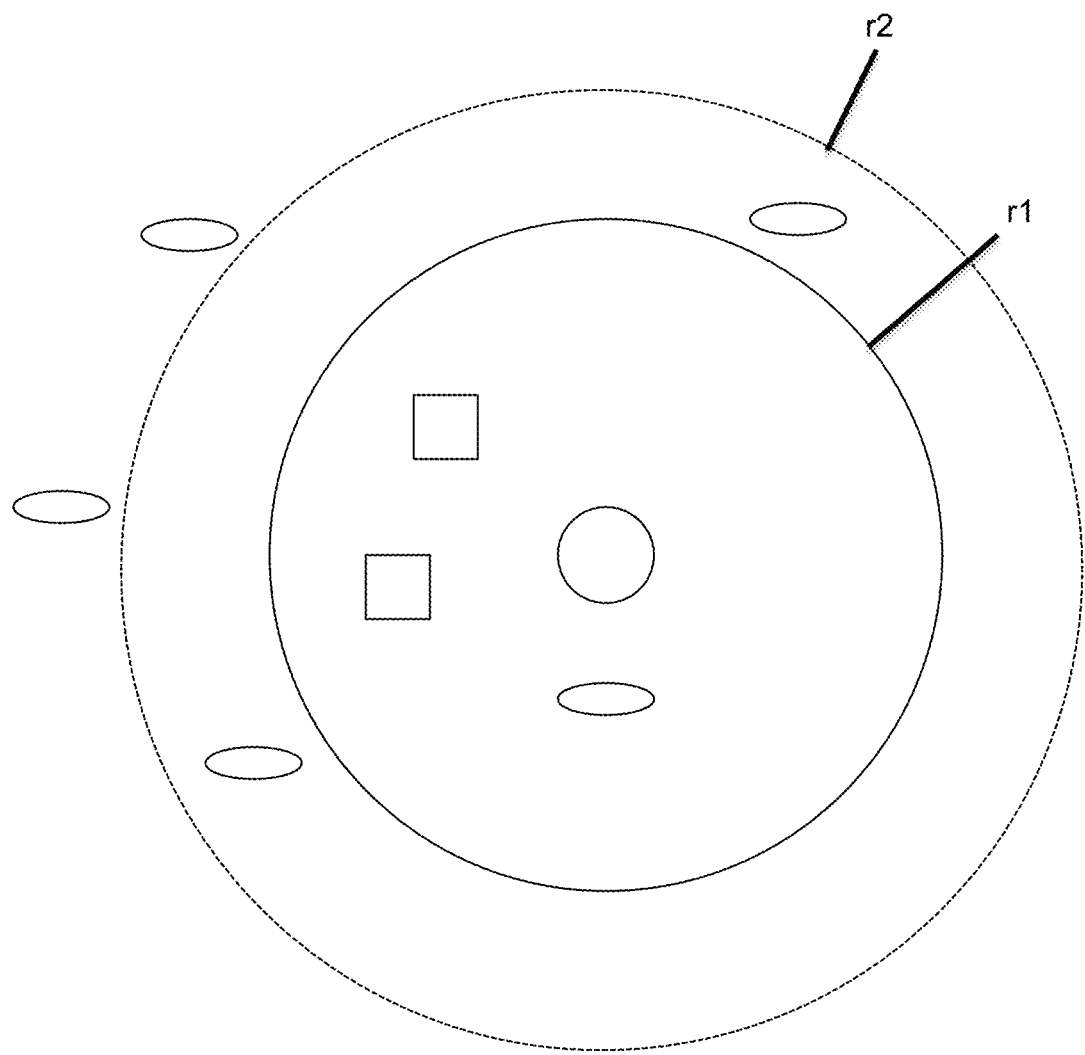
FIG. 12 illustrates a graph of K-nearest Neighbor for clusters.

FIG. 12 illustrates a graph of K-nearest Neighbor for clusters. In this figure, a sub-set of a medical image slice is examined to illustrate application of KNN. The overall purpose is accurately classify a small element of tissue at hand which will then contribute to more accurate segmentation. The K-distance (i.e., concentric circles solid and dashed is established, e.g., by the radiologist) is shown to other tissue elements and this contributes to determination of the tissue type for the tissue. Depending on the radius selected, the tissue type may vary as illustrated. A first radius, r1, contains one oval. A second radius, r2, contains 3 ovals. Such principles can be utilized for classification of the small circle inside of radius r1 and r2.

Figure 13A:
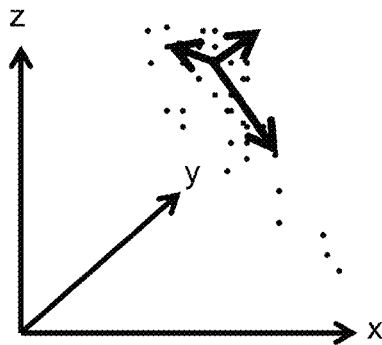
FIG. 13A illustrates an example graph with vectors derived from Principal Component Analysis (PCA) of the structure of breast micro calcifications of a linear-like structure.

FIG. 13A illustrates an example graph with vectors derived from Principal Component Analysis (PCA) of the structure of breast micro calcifications of a linear-like structure. The structure of micro calcifications within the breast can be indicative of impending cancer—or just a natural occurrence representing no danger to the patient. The structure is very difficult to discern from 2D slices and requires scrolling back and forth multiple times while the radiologist tries to formulate a mental picture of the underlying from seeing a few white dots slice N and a few more in different X-Y locations on slice N+2 some at other locations on slice N+3. Are these connected according to a tree-like structure? Recognize that the tree-like structure could be ascending or descending and slanted left or right. Are the micro calcifications random spaced with no particular pattern? Making the correct diagnosis is a major challenging problem for the radiologist. If non-micro calcification tissue were segmented and filtered and PCA applied there would be a set of plotted micro calcification points plotted and principal vectors as a result. In this figure, the points and principal were derived from a tree like structure. Note that the tree structure can literally be pointed in any direction and whether a micro calcification on slice N is somehow connected to a micro calcification on slice N+2 to another micro calcification on slice N+3 can require multiple scrolling back and forth between slices. In this figure example X-Y-Z locations for micro calcifications are plotted and two PCA vectors are shown. The fact that PCA one vector is significantly longer/stronger than PCA vector two lengths/strengths is indicative of a tree structure. In this example the tree was descending toward the right and toward the X-axis. Knowledge of the potential presence and the direction which the structure is pointing will significantly assist in smart scrolling to properly connect the micro calcification dots and verify if, in fact, a structure indicative of cancer is present. Text box 1300 is shown.

Figure 13B:
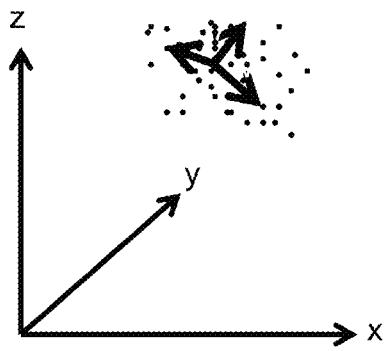

FIG. 13B illustrates an example graph with vectors derived from Principal Component Analysis (PCA) of the structure of breast micro calcifications of a cluster-like. Note that all three vectors are short. In this figure, the micro calcifications are plotted in the same manner as FIG. 13*a*. In this case, the micro calcifications in the patient were randomly scattered within the breast. When PCA was applied multiple small vectors resulted which were of approximately the same length/strength. Knowledge of these vectors will significantly assist in smart scrolling to properly connect the micro calcification dots and verify if, in fact, a random structure indicative of a benign condition. Text box 1301 is shown.

Figure 14:
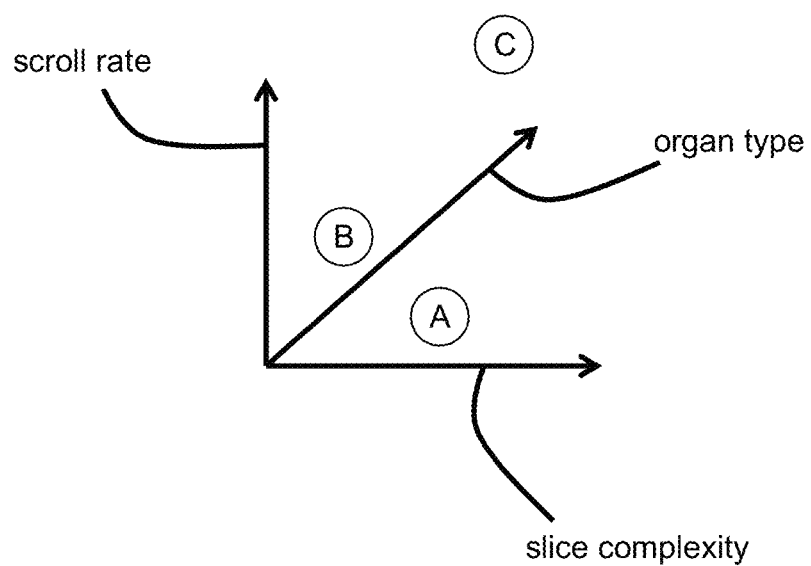
FIG. 14 illustrates an example of Linear Discriminant Analysis (LDA) applied to determine pause duration as a function of organ type and slice complexity.
Figure 15:
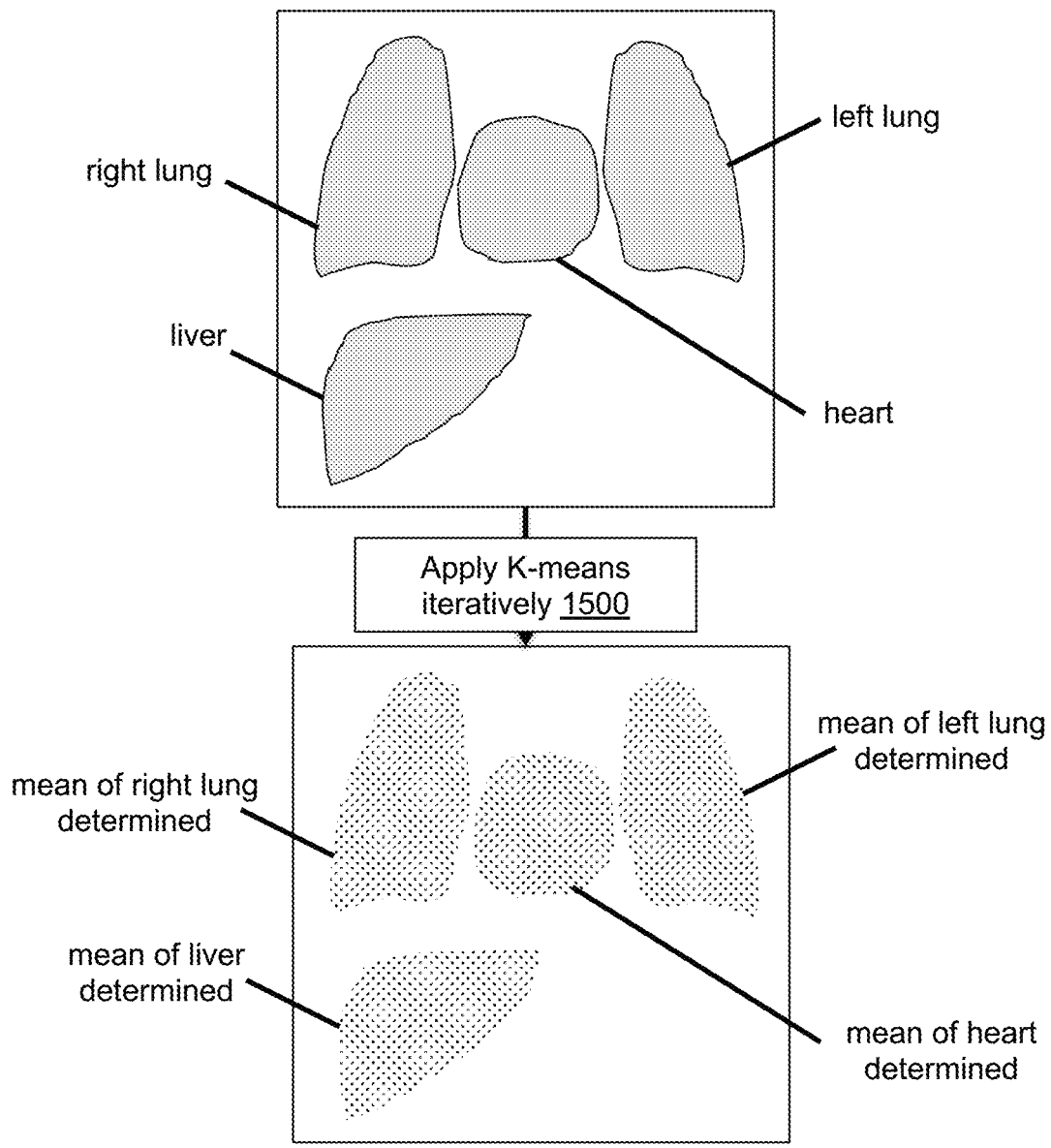
FIG. 15 illustrates an example of K-means to determine clusters.
Figure 16:
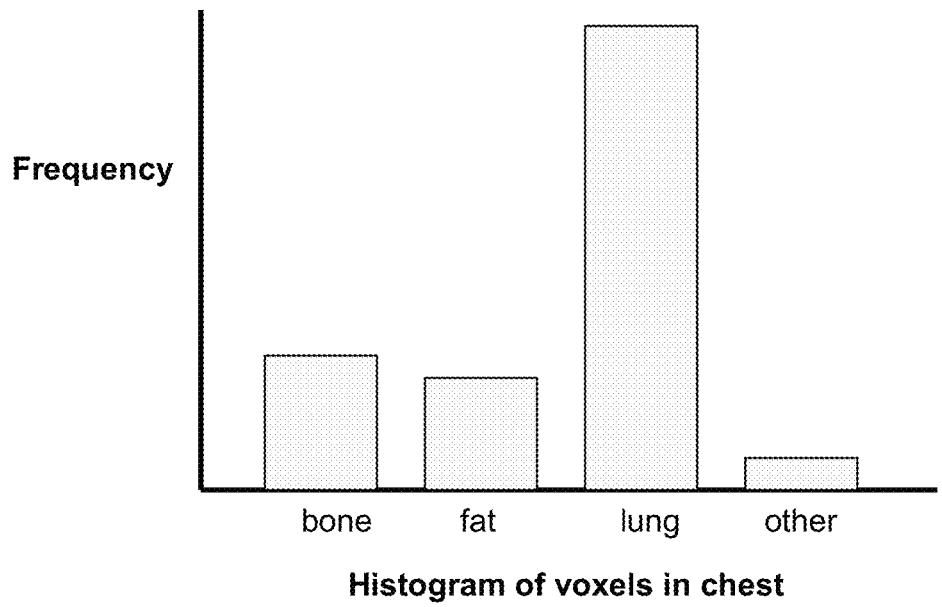
FIG. 16 illustrates an example of anomaly detection using outlier detection.

FIG. 14 illustrates an example of Linear Discriminant Analysis (LDA) applied to determine pause duration as a function of organ type and slice complexity. LDA takes two factors into account and from this determines a third, dependent factor. This figure shows a 3D plot of medical image complexity (X-axis) vs. organ type (Y-axis) and resulting pause duration (Z-axis). If the pancreas were the checklist item at hand and if the image slice being examined contained pancreas tissue and the image was of high complexity, then the automatic smart scrolling pause duration would be adjusted accordingly whereas, other types of organs and their associated complexity would have their own respective scrolling pause duration FIG. 15 illustrates an example of K-means to determine clusters. Problem: in the torso, how do you segment the lung, heart and liver? (Each of these have different tissue properties (e.g., Hounsfield units) and textures). This figure first illustrates a portion of the upper torso with the purpose of segmenting the internal organs into three groupings: heart, lungs, and liver. This figure shows a plot of the number of tissue elements within a set of (or frequency of occurrence thereof) by Hounsfield Unit value of a particular pixel/voxel. (Note that on an image slice the tissue elements are shown as pixels with differing gray scales which are directly related to the Hounsfield Unit. Then, given K-means clustering algorithm is applied 1500, the cluster of each of the organs of interest will be identified and the means thereof determined. Segmentation and filtering can then follow. Collectively, this filtration and segmentation will speed the scrolling process through helping the radiologist focus only on the heart without distraction of having some eye fixation points being eternal to this checklist item of interest.

Tumors in the initial stages may be hard to detect due to their small size and have a gray scale such that it blends in with adjacent tissue. Saccadian eye movement may not fixate on a small cluster of this type and thus the tumorous might go undetected. One type of artificial intelligence algorithms to increase the probability of anomaly detection is through finding outliers. This figure depicts a histogram of a slice of lung tissue wherein a small cluster of tumorous tissue is present. Cluster analysis-based outlier detection could signal smart scrolling to the outlier location for inspection by the radiologist. The smart scrolling could rapidly move to the slice(s) or voxel(s) to which contain these outlier tissue and, thus, expedite the radiologist review.

FIG. 17A illustrates an example Artificial Neural Networks (ANN) applied to breast tumors. ANNs attempts to replicate the way the brain in such tasks as facial recognition and have shown to be ways of pattern recognition. The pattern of a tumor within a breast can be indicative as to whether it is cancerous or benign. Tumors with speculated surfaces are generally indicative of cancer. The speculations, however, can be quite small and hard to detect. ANNs may prove to be good at distinguishing speculated surfaces. This figure shows a blow up of a cancerous breast tumor with spiculations protruding from the surface. The smart scrolling could rapidly go to such a tumor and zoom in for close inspection by the radiologist.

FIG. 17B illustrates an example Artificial Neural Networks (ANN) applied to breast tumors. This figure shows a blow up of a breast tumor which is benign. ANNs applied may detect a distinct pattern of a breast tumor with smooth, lobulated surfaces. The smart scrolling could rapidly go to such a tumor and zoom in for close inspection by the radiologist.

Figure 18A:
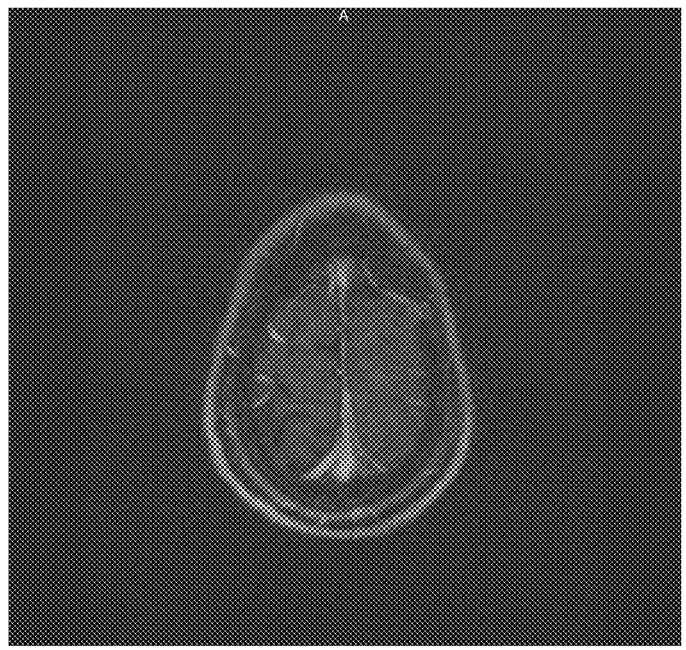
FIG. 18A illustrates an example of a slice with a small area with relevant patient data.

FIG. 18A illustrates an example of a slice with a small area with relevant patient data. When the area within a slice which contains relevant is small, the required eye fixation points for adequate radiologist review reduces accordingly. Artificial intelligence could rapidly count the number of pixels with relevant data (e.g., areas within the image slice that were either black or white would not be included in the count-only pixels with gray scales other than black or white). The pause duration would also reduce for smart scrolling.

Figure 18B:
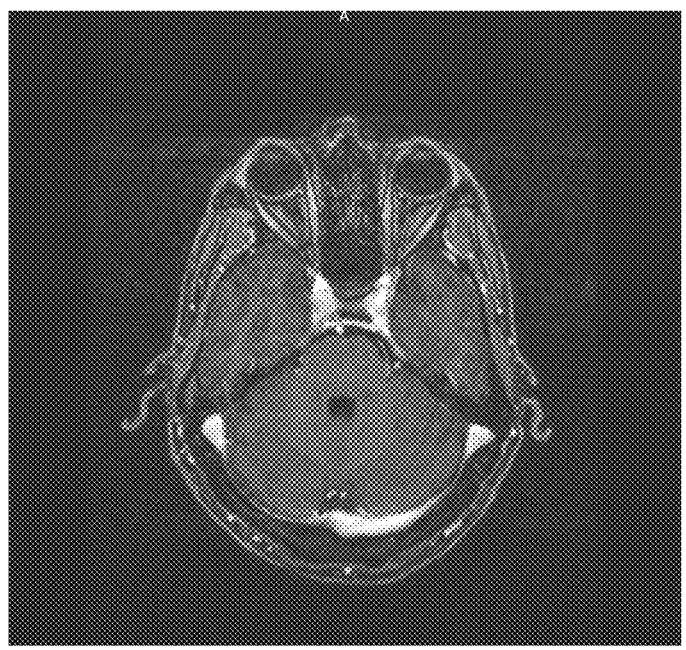
FIG. 18B illustrates an example of a slice with a large area with relevant patient data.

FIG. 18B illustrates an example of a slice with a large area with relevant patient data. Conversely, when the area within a slice which contains relevant is large, the required eye fixation points for adequate radiologist review increases accordingly. The pause duration would also increase for smart scrolling.

FIG. 19 illustrates factors in determining the amount of time spent per image. Factors include: complexity of image; size of image; probability of image containing pathology; shape of structures within image; whether structures displayed on images contained pathology on a previous medical imaging examination; whether structures displayed on images are correlated to laboratory abnormalities; whether structures displayed on images are correlated to physical examination abnormalities; whether structures displayed on images are correlated to pharmacotherapy; whether structures displayed on images are correlated to an abnormality identified by an artificial intelligence algorithm or a computer aided detection algorithm; whether structures displayed on images in said image set are correlated to a diagnosis; eye tracking metrics; a checklist item; characterizing a structure by performing at least one of the group consisting of: Naive Bayes; Support Vector Machine; K-nearest neighbors; K-means clusters; principal component analysis; artificial neural networks; linear regression; logistic regression; linear discriminant analysis; and decision tree analysis; an orientation of a structure; a spatial relationship between at least 2 segmented structures; and, a relationship between consecutively displayed images.

What is claimed is:

1. A method of reviewing images comprising:
   performing an analysis of an image set
   wherein said image set comprises a medical imaging examination, and
   wherein said analysis comprises determining probabilities of containing at least one pathology for structures displayed on images in said image set;
   determining amounts of time to display images within said image set
   wherein said amount of time is based on at least probabilities of containing at least one pathology for structures displayed on an image,
   wherein a first structure has first probability of containing at least one pathology on a first image,
   wherein a second structure has second probability of containing at least one pathology on a second image,
   wherein said second probability is higher than said first probability,
   wherein said first image is displayed for a first amount of time,
   wherein said second structure is displayed for second amount of time, and
   wherein said first amount of time is less than said second amount of time;
   displaying said first image for said first amount of time; and
   displaying said second image for said second amount of time.

2. The method of claim 1 further comprising wherein said analysis comprises determining sizes for structures displayed on images in said image set.

3. The method of claim 1 further comprising wherein said analysis comprises determining complexity levels on images in said image set.

4. The method of claim 1 further comprising wherein said analysis comprises determining shapes of structures displayed on images in said image set.

5. The method of claim 1 further comprising wherein said analysis comprises determining whether structures displayed on images in said image set contained pathology on a previous medical imaging examination.

6. The method of claim 1 further comprising wherein said analysis comprises determining whether structures displayed on images in said image set are correlated to laboratory abnormalities.

7. The method of claim 1 further comprising wherein said analysis comprises determining whether structures displayed on images in said image set are correlated to physical examination abnormalities.

8. The method of claim 1 further comprising wherein said analysis comprises determining whether structures displayed on images in said image set are correlated to pharmacotherapy.

9. The method of claim 1 further comprising wherein said analysis comprises determining whether structures displayed on images in said image set are correlated to an abnormality identified by an artificial intelligence algorithm or a computer aided detection algorithm.

10. The method of claim 1 further comprising wherein said analysis comprises determining whether structures displayed on images in said image set are correlated to a diagnosis.

11. The method of claim 1 further comprising wherein said analysis comprises determining eye tracking metrics.

12. The method of claim 1 further comprising using determined amounts of time to display images within said image set to control scrolling rate.

13. The method of claim 1 further comprising using determined amounts of time to display images within said image set to optimize scrolling rate of image slices.

14. The method of claim 1 further comprising using determined amounts of time to display images within said image set to optimize rotation rate for volume rendered images.

15. The method of claim 1 further comprising wherein said analysis comprises determining checklist item.

16. The method of claim 1 further comprising wherein said analysis comprises characterizing a structure by performing at least one of the group consisting of:
   Naive Bayes;
   Support Vector Machine;
   K-nearest neighbors;
   K-means clusters;
   principal component analysis;
   artificial neural networks;
   linear regression;
   logistic regression;
   linear discriminant analysis; and
   decision tree analysis.

17. The method of claim 1 further comprising wherein said analysis comprises characterizing an orientation of a structure.

18. The method of claim 1 further comprising wherein said analysis comprises characterizing a spatial relationship between at least 2 segmented structures.

19. The method of claim 1 further comprising wherein said analysis comprises characterizing a relationship between consecutively displayed images.

20. An apparatus comprising:
    a processor; and a non-transitory memory having computer-executable instructions stored thereupon which, when executed by the processor, cause the processor to perform:

performing an analysis of an image set
- wherein said image set comprises a medical imaging examination, and
- wherein said analysis comprises determining probabilities of containing at least one pathology for structures displayed on images in said image set;

determining amounts of time to display images within said image set
- wherein said amount of time is based on at least probabilities of containing at least one pathology for structures displayed on an image,
- wherein a first structure has first probability of containing at least one pathology on a first image,
- wherein a second structure has second probability of containing at least one pathology on a second image,
- wherein said second probability is higher than said first probability,
- wherein said first image is displayed for a first amount of time,
- wherein said second structure is displayed for second amount of time, and
- wherein said first amount of time is less than said second amount of time;

displaying said first image for said first amount of time; and displaying said second image for said second amount of time.

* * * * *